United States Patent [19]
Gion et al.

[11] Patent Number: 4,715,849
[45] Date of Patent: Dec. 29, 1987

[54] METHOD FOR EASILY DRAWING BLOOD FROM ARM OR LEG

[75] Inventors: Hidenori Gion; Takumi Yoda, both of Okayama; Yasuzo Kirita, Toyonaka; Kazuhito Zaima, Saijo; Noriyuki Kurata, Takamatsu, all of Japan

[73] Assignee: Kuraray Co., Ltd., Kurashiki, Japan

[21] Appl. No.: 832,524

[22] Filed: Feb. 21, 1986

[30] Foreign Application Priority Data

Feb. 26, 1985 [JP] Japan .................................. 60-38563

[51] Int. Cl.⁴ .............................................. A61B 17/12
[52] U.S. Cl. ...................................... 604/52; 128/327
[58] Field of Search .................. 128/327, 64; 604/4–6, 604/52

[56] References Cited

U.S. PATENT DOCUMENTS

| | | | |
|---|---|---|---|
| 4,086,924 | 5/1978 | Latham | 604/6 |
| 4,294,261 | 10/1981 | Baker et al. | 128/327 X |
| 4,469,099 | 9/1984 | McEwen | 128/327 |
| 4,548,198 | 10/1985 | Manes | 128/327 |

*Primary Examiner*—Michael H. Thaler
*Attorney, Agent, or Firm*—Kramer, Brufsky & Cifelli

[57] ABSTRACT

An apparatus for easily drawing blood from arm or leg, which is provided with an inflatable air bag to be wound around the arm or leg and to intermittently squeeze a part of the arm or leg in a fixed length. Control over inflation and contraction of the air bag by means of an electronic circuit permits free and precise change of a length of time for inflating or contracting the air bag as well as pressure in the air bag. An apparatus according to this invention for drawing blood from swollen vein extending within a part between the air bag and the tip of arm of leg can increase a quantity of blood to be drawn. Therefore, this apparatus is generally used together with an extracorporeal blood circulation and treating apparatus.

3 Claims, 8 Drawing Figures

METHOD FOR EASILY DRAWING BLOOD FROM ARM OR LEG

BACKGROUND OF THE INVENTION

1. Field of the Invention

This invention relates to an apparatus for easily drawing blood from the patient's arm or leg. The apparatus of this invention can increase the quantity of blood drawn per unit time and, therefore, is particularly suitable for joint use with blood treatment apparatus for plasma collection requiring a long period of time in blood drawing.

2. Description of Prior Art

A method generally employed for easy blood drawing from a patient's body is to use a tourniquet made of rubber tube. The tourniquet is tightly wound around the patient's arm or leg. Blood is drawn from the swollen vein in the arm between the tourniquet and the tip of arm or leg. In most cases, blood is drawn from the bent part of the elbow. In the case of extracorporeal circulation blood treatment, treated blood is returned to the patient's body through either the other arm freed from the tourniquet or a part lying upstream of the tourniquet.

Such a method as using the tourniquet is well known to those skilled in the art. However it is known that the method is inapplicable to extracorporeal blood circulation continuing for a long time by reason of the possible danger of of toxic substances remaining in the vein constricted by the tourniquet. Accordingly, when using the tourniquet, it is necessary to loosen the tourniquet periodically and then re-start extracorporeal blood circulation. However, in practice, adjustment of pressure for tightening the tourniquet during blood drawing is difficult.

On the other hand, a method of pressing the vein with a bag-like band, instead of the tourniquet, wound around the patient's arm or leg and inflated with air is now employed (Japanese Patent Laid-open No. 12195/1983 and others). According to this method, the bag-like band is connected to a tank containing pressurizing gas such as nitrogen or Freon by a tube and the pressurizing gas is fed into the bag-like band by opening an electrically driven valve connected to the tube. This method, however, is attended by the danger of toxic substances remaining in the pressed part of the vein due to constant inflation of the band, a situation similar to the application of a tourniquet. In addition, the use of pressurizing gas is dangerous to handle and causes a problem in that a sure and safe adjustment of pressure requires a large and costly apparatus.

SUMMARY OF THE INVENTION

An object of this invention, therefore, is to provide an apparatus for drawing blood easily and safely from the patient's arm or leg.

The apparatus of this invention intermittently presses the patient's vein for increasing a quantity of blood to be drawn while inflating and contracting a bag-like band wound around the patient's arm or leg.

The apparatus of this invention is composed of a pneumatic pump; a bag-like band to be wound around the patient's arm or leg which provides for changing the pressure there applied by means of pressure of air supplied from the abovesaid pump; a valve for outwardly discharging or retaining the compressed air generated by driving of the abovesaid pump; a circuit for controlling an interval of pressurizing of the bag-like band and of air discharge therefrom, which emits signals for periodically closing the abovesaid valve and, at the same time, emits signals for driving the pump; a circuit for controlling the pressure in the bag-like band, which emits signals for driving the pump, while comparing the pressure in the bag-like band with a preset level of pressure, until the bag pressure reaches the preset level; and a coincidence circuit which emits pump driving signals to the pump driving circuit only when signals emitted from the circuit for controlling an interval of pressurizing of the bag-like band and air discharge therefrom and those emitted from the circuit for controlling the bag pressure are all pump driving signals.

DETAILED DESCRIPTION OF THE INVENTION

Figure 1:
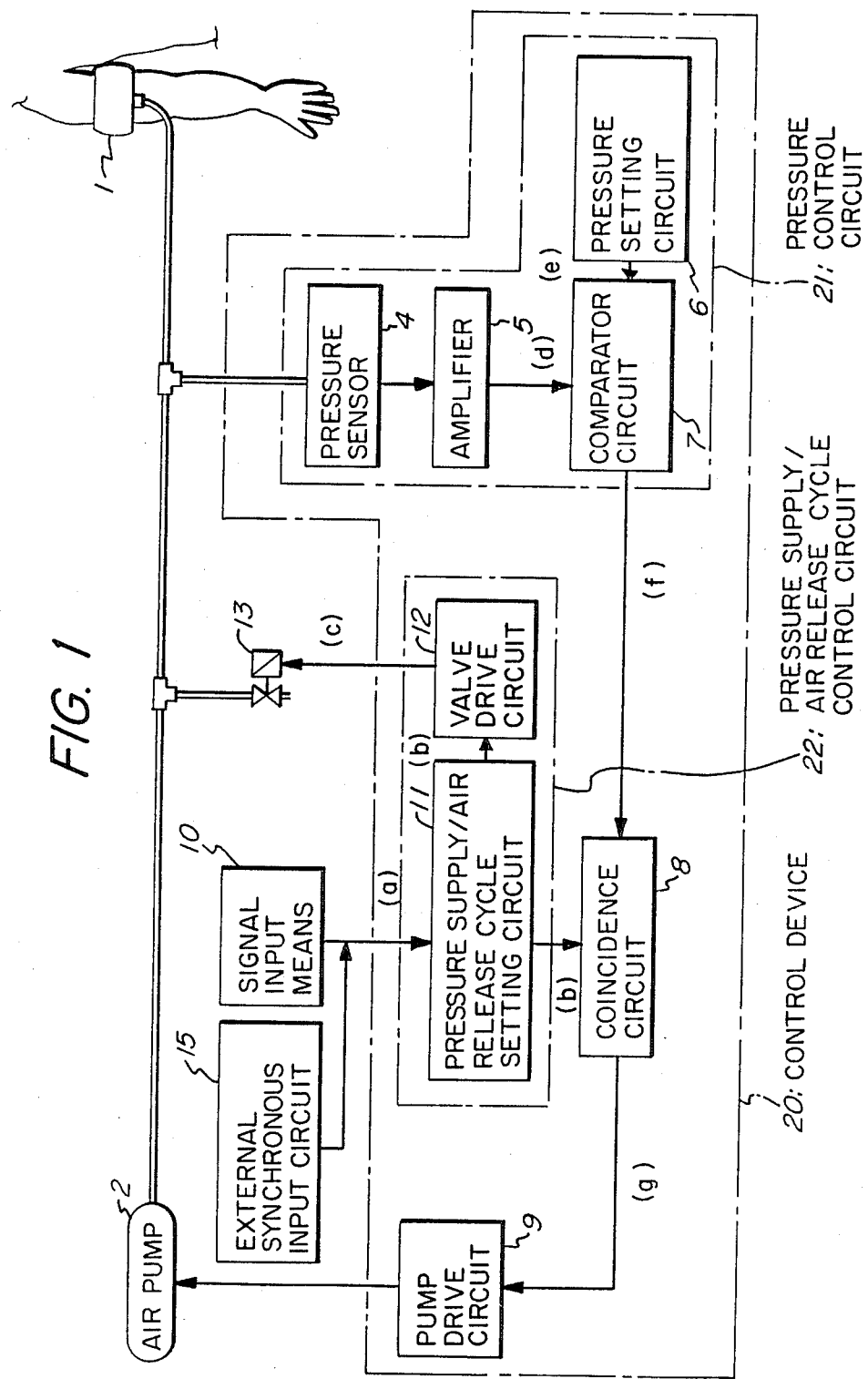
FIG. 1 is a schematic block diagram of an apparatus as an embodiment of this invention.

FIG. 1 is a schematic block diagram of an apparatus according to this invention.

An apparatus of this invention comprises such main parts as: a bag-like band 1 pressing the periphery of the patient's arm or leg which applies and removes pressure to and from the patient's vein while periodically repeating inflation and contraction thereof; a pneumatic pump 2 actuated only when inflating the bag-like band, and feeding air into the bag-like band through the conduit 14; a valve 13 for feeding air into the air bag or discharging air therefrom while discharging or keeping pressurized air generated by driving of the abovesaid pump; and a control device 20 emitting opening/closure signals to the abovesaid valve and drive/stop signals to the pneumatic pump.

The bag-like band 1 is an inflatable slender air bag to be wound around the patient's arm or leg and capable of squeezing a part of the arm or leg in a fixed length, which is generally a cuff for blood pressure measurement used in sphygmomanometers sold on the market. The width of the cuff for blood pressure measurement is usually 14 cm for adults.

When pricking one arm with two needles for drawing and returning of blood, particularly, in the case of hemodialysis using shunts, preferable it is to apply a cuff to a part of the arm between the blood drawing needle and blood returning needle for easier blood returning. In this case, a cuff of small width, usually, 4 to 9 cm, is used.

A pneumatic pump 2 is any of those which are capable of obtaining a flow quantity of 2 l/min or more and pressure of 100 mmHg or more, such as a diaphragm pump and bellows pump of small size. The pump is not always driven throughout the use of this apparatus but, when required, driven through a control device that will be described later. Air fed from the pump 2 passes through the conduit 14 and inflates the cuff 1.

A valve 13 connected to the conduit 14 is opened and closed by electric or pneumatic signals and usually an electromagnetic valve. The valve 13 is opened upon stoppage of the pneumatic pump 2 and discharges air from the cuff for contraction thereof. This valve 13 is of such type as being normally in the open position and closed when electrically powered. A control device 20 emitting opening/closure signals toward the valve 13 and drive/stop signals toward the pneumatic pump 2 is composed of a pressure control circuit 21 for controlling the cuff pressure and a pressurizing/discharge interval control circuit 22 for periodically opening and closing the valve 13.

A pressure control circuit 21 for controlling the cuff pressure is composed of: a pressure sensor 4 (usually, a semiconductor pressure transducer and a differential transformer type pressure transducer) which senses the air pressure in the conduit 14 and converts pressure energy into electric signals; an amplifier 5 for amplifying signals sensed by the abovesaid sensor; a pressure setting circuit 6 for setting the cuff pressure; and a comparator circuit 7 which compares amplified signals transmitted from the pressure sensor with the pressure signals set by the pressure setting circuit 7 emits pump driving signals until the cuff pressure reaches a set level of pressure 7 and emits pump stopping signals when the cuff pressure reaches the set level.

Figure 3:
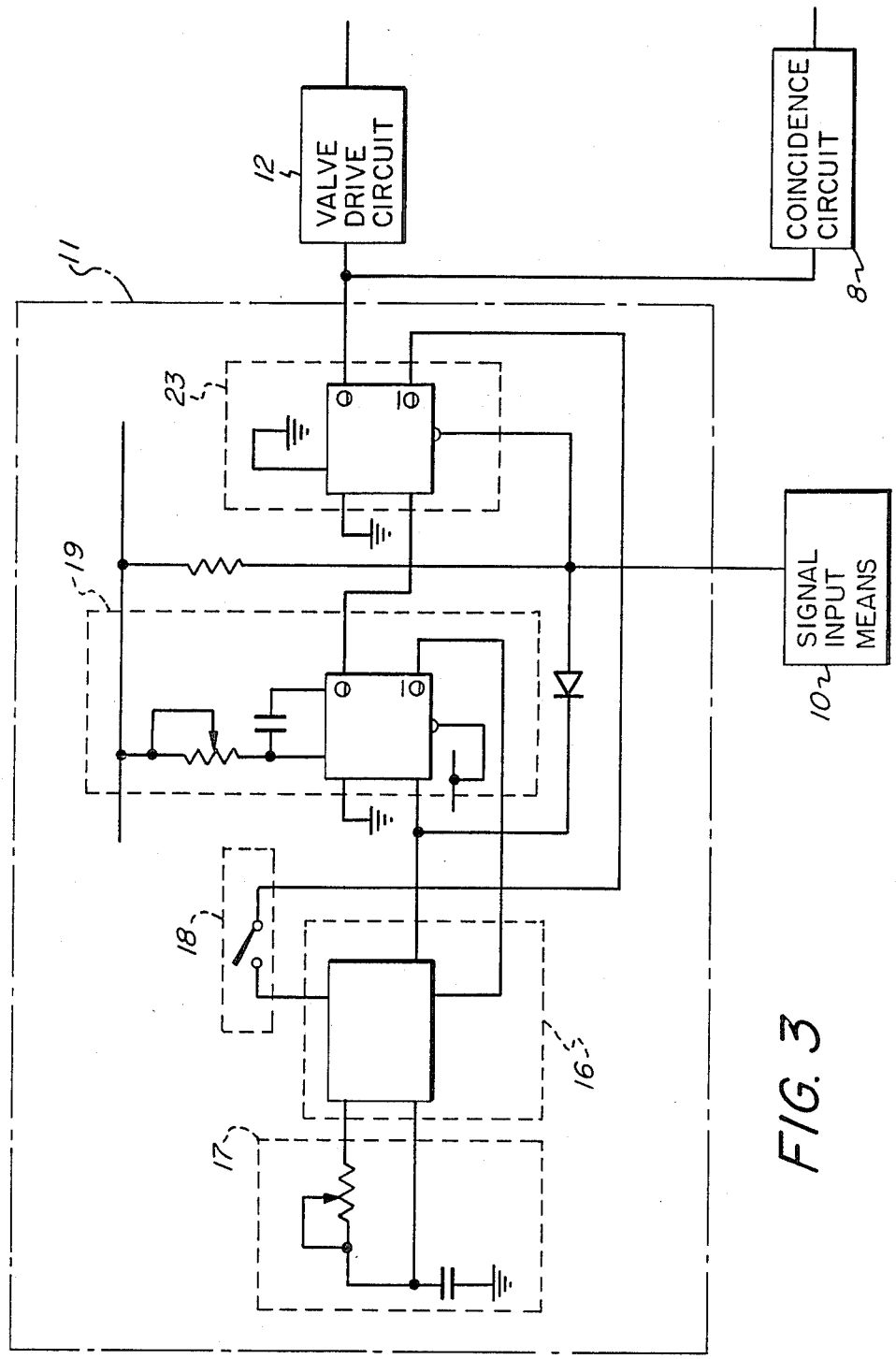
FIG. 3 is an electric circuit as an embodiment of the pressurizing/air-discharge interval setting circuit shown in FIG. 1.

On the other hand, the pressurizing/discharge interval control circuit 22 sets periods of time inflating (pressurizing) the cuff 1 and releasing air pressure (contraction) for opening and closing the valve 13 with the valve opening/closing signals emitted therefrom. This circuit 22 comprises a circuit 11 for setting a time for inflating and contracting the cuff and a valve driving circuit 12 for opening and closing the valve 13 in response to signals from the abovesaid circuit 11. A concrete example of a circuit 11 for setting a time of cuff inflation and contraction is shown in FIG. 3. In FIG. 3, the oscillator and divider circuit 16 generates the square wave according to the cuff pressing interval which is adjusted by the interval time set circuit 17. 18 is the mode switch which is the part of the interval time set circuit 17, and decides the cuff pressing mode (continuous pressing/intermittent pressing). The pressing/releasing time control circuit 11 decides the cuff pressing time and the cuff releasing time (fixed by the releasing time set circuit 19).

A logic circuit 23 emits ON/OFF signals to the coincidence circuit 8 and valve driving circuit 12.

Pump driving signals are emitted from the pressurizing/discharge interval setting circuit 11 to the valve driving circuit 12 and further to the coincidence circuit 8 as shown in FIG. 1. These pump driving signals are compared with those emitted from the pressure control circuit 21 and, only when they are pump driving signals together, pump driving signals are emitted to the pump driving circuit 9, thereby causing the pump to be driven. When at least one of these two kinds of signals is for pump stopping (cuff contraction), no signals are emitted from the coincidence circuit 8 to the pump driving circuit 9, thereby causing the pump to be stopped.

For any of the abovesaid circuits, various kinds of known circuits may be used.

Figure 2:
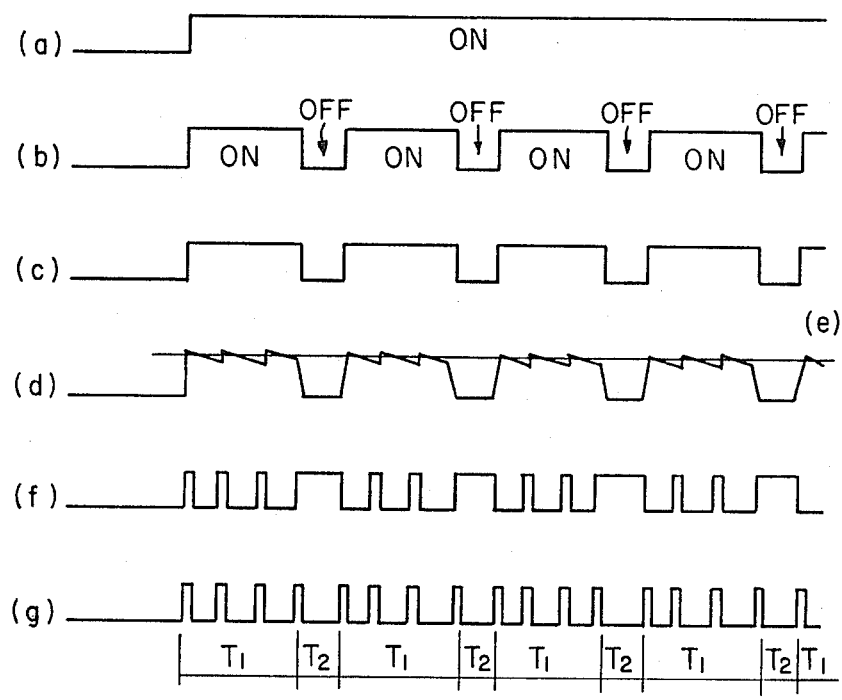
FIG. 2 is a time chart representing the performance of every part of the above apparatus.

Performance of the apparatus of this invention will be described with reference to a time chart shown in FIG. 2. At first, ON signals (a) are emitted from signal input means, for example, an ON-OFF button 10, to the abovesaid pressurizing/discharge interval control circuit 22. When synchronizing ON signals with external signals, it is necessary to further provide an external synchronous input circuit 15. If so provided, valve opening/closing signals (b) are periodically emitted from the pressurizing/discharge interval setting circuit 11 for setting a period of time $T_1$ for inflation and that $T_2$ for contraction to the valve driving circuit 12. The valve driving signals (b) are emitted toward the coincidence circuit 8, too, and compared with signals (f) emitted from the pressure control circuit 21 at the coincidence circuit 8.

On the other hand, the cuff pressure emits pump driving signals (f) until signals (d), which are emitted from the pressure sensor 4, amplified by the amplifier 5, and compared with a preset pressure level (e) by the comparator circuit 7, reaches this pressure level (e). The cuff used in the sphygmomanometer is made of cloth and attended by air leakage which also occurs in the pneumatic pump and, therefore, pump driving signals are intermittently emitted for constantly maintaining the cuff pressure at a preset level during the cuff inflation time $T_1$. Signals (f) from the pressure control circuit 21 and those (b) from the pressurizing/discharge interval setting circuit 11 are compared with each other by the coincidence circuit 8 and, only when these two kinds of signals are all pump driving signals, pump driving signals (g) are emitted to the pump driving circuit 9 for driving the pump. When at least one of the two kinds of signals is not the pump driving one (pump stoppage), no signals are transmitted from the coincidence circuit to the pump driving circuit. Accordingly, during the time as above, the pump is not driven, that is, the cuff contracts. This apparatus detects abnormal pressure, if any, with a pressure sensor and, while emitting alarm in response to detection signals, stops operating so as to discharge air from the cuff. Control parts of the pressurizing/discharge interval setting circuit 11 and the coincidence circuit 8 may jointly be controlled by means of a microcomputer and adapted to operate according to the predetermined program.

Figure 4:
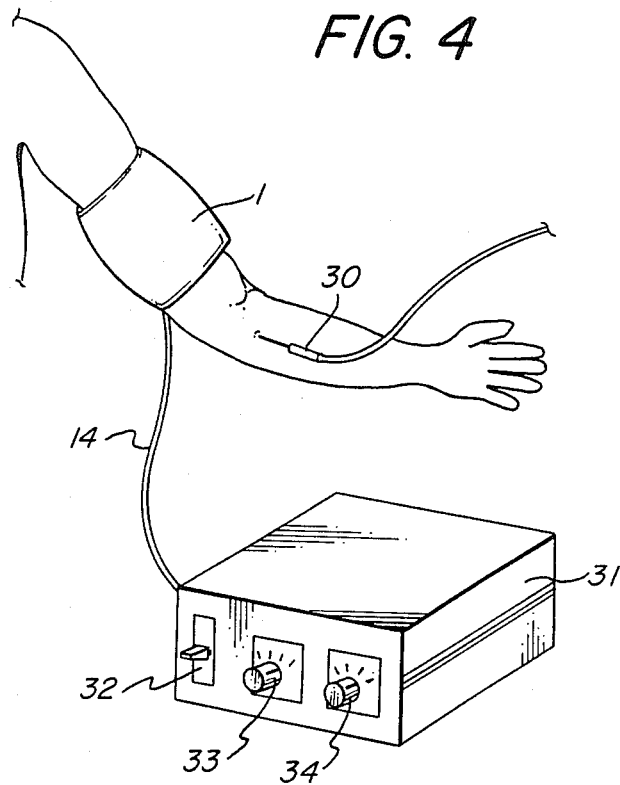
FIG. 4 is a perspective view of an apparatus of this invention attached to the patient's body.

The above-mentioned apparatus can easily be fitted on a patient from whom blood is to be drawn. FIG. 4 shows an example where the apparatus is fitted on the patient, wherein the cuff is fitted on an upper arm of the patient. An injection needle or catheter for returning blood to the patient's body is arranged near the elbow. The reference numeral 31 indicates a monitor containing the pneumatic pump 2, valve 13, and control device 20 as shown in FIG. 1, the monitor 31 being connected to the cuff 1 with a conduit 14 made of neoprene rubber. The monitor used in this invention is, for example, 15 cm wide, 8 cm high, and 16 cm long, and provided with a power switch 32 disposed in the front side, dial 33 for setting the pressing time within the range from 0 to 10 sec and pressure setting dial for setting a cuff pressure within the range from 0 to 150 mmHg. Further, in this apparatus, the air discharge time is set at 1.5 sec in the monitor beforehand and adapted to be changeable by handling from outside. The air discharge time is usually set within the range from 1 to 3 sec. A length of time shorter than 1 sec leads to a possibility that pressing is performed earlier than complete discharge of air from the cuff whereas that longer than 3 sec results in a low rate of increase in the quantity of blood to be drawn per unit time.

Figure 5:
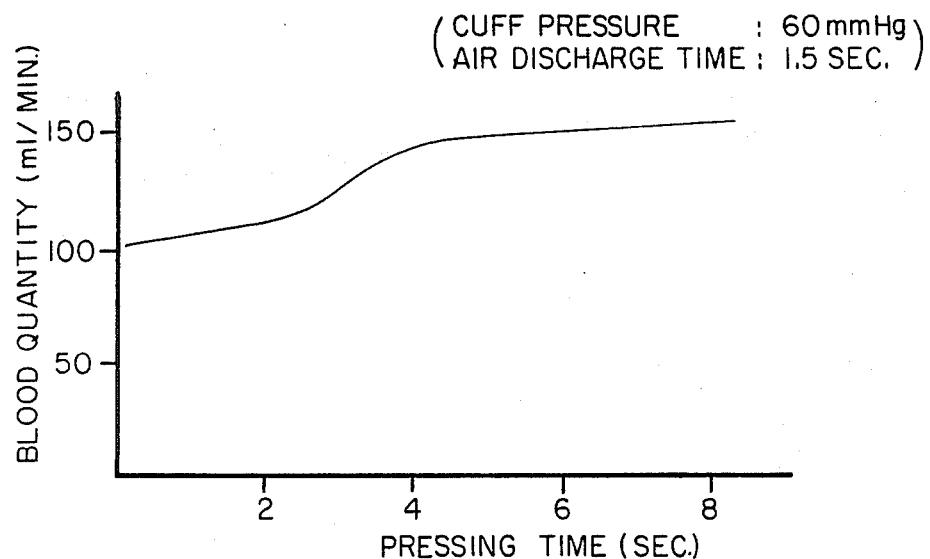
FIG. 5 is a graph showing the relation between a length of time for pressurizing the cuff and the quantity of let blood.
Figure 6:
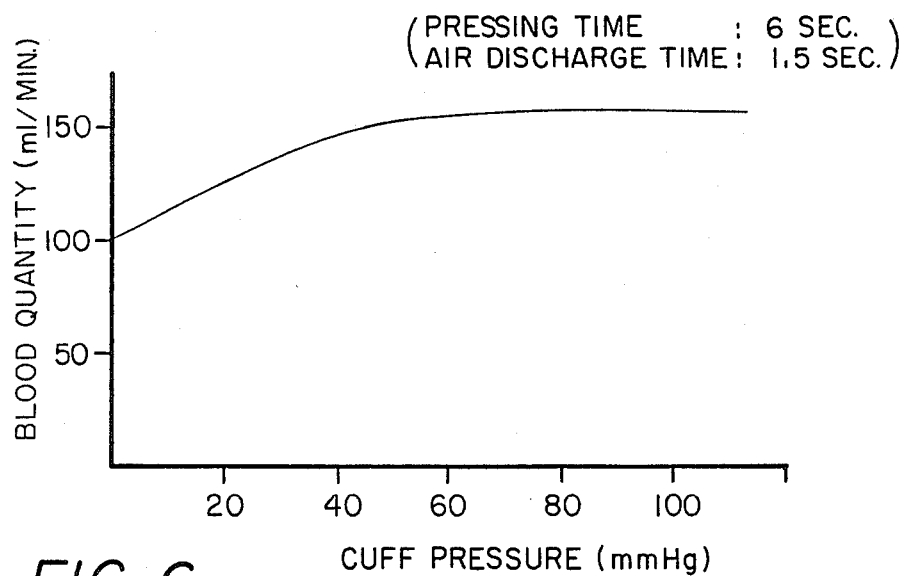
FIG. 6 is a graph showing the relation between the pressure for pressurizing the cuff and the quantity of let blood.

An apparatus of this invention is used at a cuff pressure ranging from 30 to 150 mmHg and the pressing time ranging from 3 to 10 sec by the use of a cuff. Such conditions have been set for the following reasons. The result of examining the relation between the length of pressing time and the drawn blood quantity at a cuff pressure of 60 mmHg and the air discharge time of 1.5 sec are shown in FIG. 5. As apparent from FIG. 5, no increase in quantity of drawn blood is apparent at the pressing time shorter than 3 sec. At the pressing time longer than 10 sec, the blood quantity is in equilibrium and does not increase further. The result of examining the relation between the cuff pressure and the quantity of drawn blood under the above-said conditions is shown in FIG. 6. As is apparent from FIG. 6, no increase in blood quantity is recognized at the cuff pressure lower than 30 mmHg. When the cuff pressure was 150 mmHg or higher, the patient felt strong pressure and, in addition, no increase in quantity of drawn blood was shown. From the above results, it has been found that, when setting the cuff pressure at 30 to 150 mmHg and the pressing time using the cuff at 3 to 10 sec, the use of this apparatus improves the flow quantity of blood in a vein to 70 to 80 ml/min as compared with 40 to 50 ml/min at the time of blood drawing without the use of any tourniquet.

Figure 7:
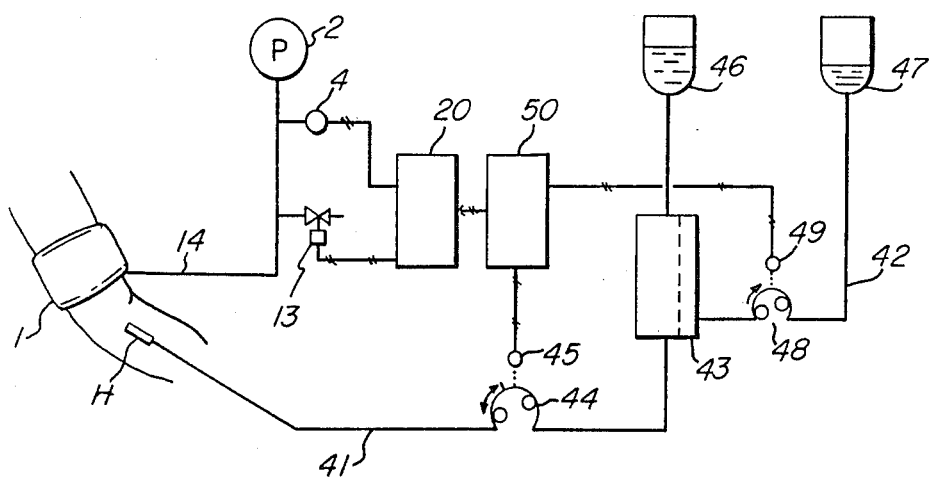
FIG. 7 is a flow chart showing an example using an apparatus of this invention together with a plasma collection apparatus; and, FIG. 8 is a flow chart showing an example using an apparatus of this invention together with a hemodialysis apparatus.

This apparatus is not limited to the use for blood treatment and can be used, as an example, for plasma separation to separate plasma component from corpuscular components (red blood corpuscle, white blood corpuscle, and blood platelet) using centrifugal force or membrane. In the case of plasma removal operation, plasma component is drawn from the patient. A plasma removal operation for therapeutic purpose can be referred to as an example. In this case, plasma component is separated from corpuscular components of the patient. At the time of such plasma removal operation, plasma component is treated to remove certain toxic substances in the plasma and the purified plasma is continuously returned to the body of the same patient together with corpuscular components. The apparatus of this invention can also be used for hemodialysis using a comparatively small flow quantity of blood. The apparatus of this invention is controlled in association with a blood treatment apparatus and constantly operated at the time of blood drawing. At this time, an external synchronzing circuit is provided and external signals are input thereinto. For example, when the apparatus is used for collecting plasma component from blood by means of membrane separation, signals are input into the control device 20 only at the time of drawing blood. In response to the signals thus input, the cuff 1 fitted on the upper arm of the patient intermittently presses the vein of the patient. In the apparatus shown in FIG. 7, a blood flow passage 41 is provided with a membrane module 43 for separating blood discharged from the blood drawing needle H into corpuscle and plasma components, a bag 46 for reserving corpuscular component separated by the membrane module, a blood pump 44 rotatable in the right and reverse directions, and a sensor 45 for sensing the flow quantity in the blood passage, whereby separated corpuscular component is reserved in the bag 46 and the blood pump 44 is driven in the reverse direction for returning corpuscular component in the bag to the patient's body through the injection needle H.

The plasma flow passage 42 is provided with a bag 47 for reserving plasma component separated by the membrane module 43 and a sensor 49 for sensing the flow quantity in the plasma flow passage, whereby plasma component separated by the membrane module 43 is reserved in the bag 47.

The blood pump 44 stops drawing blood when receiving sensing signals from the blood flow quantity sensor 45 and rotates in the reverse direction for returning corpuscular component in the corpuscle reserving bag 46 to the patient's body. When revolutions of the blood pump 44 in the reverse direction in a fixed length of time have been detected by the timer or the like, the blood pump again rotates in the right direction for drawing blood from the patient. With the repetition of the above-said performance, a required quantity of plasma component is collected. The blood pump 44 is driven by means of the control device 50. The apparatus of this invention is of such design that signals are input from the abovesaid control device 50 into a control device 20 when the blood pump rotates in the right direction.

Figure 8:
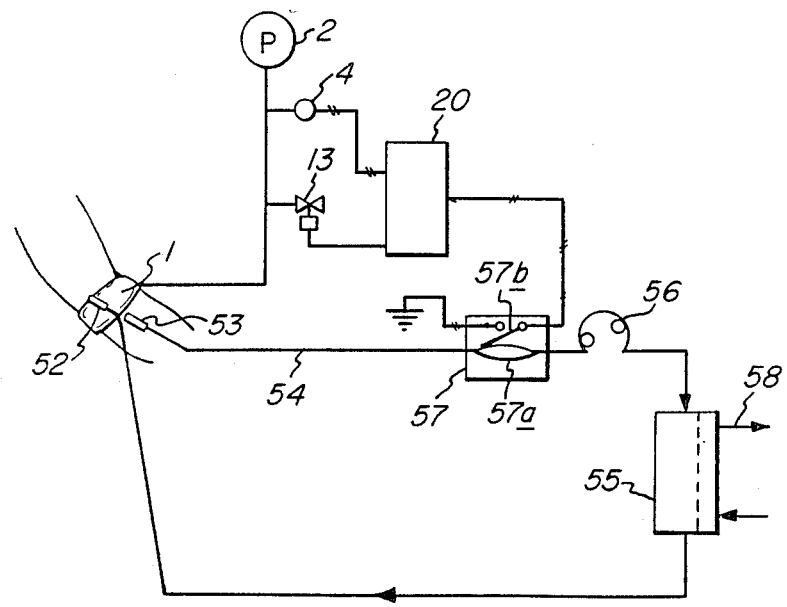

In the process of extracorporeal blood treatment, it is also possible to intermittently inflate the cuff by emitting signals when the quantity of blood drawn from the patient decreases and by inputting these signals into the control device 20. In this case, signals emitted toward the control device 20 diminish with the return of the quantity of drawn blood to the normal flow quantity. Decrease in quantity of drawn blood can be detected by, for example, a pressure sensor, usually a bag-like pillow switch, disposed upstream of the blood pump in the blood circulation flow passage and detecting the negative pressure in the flow passage. The pillow switch is always fixed to the extracorporeal blood circulation passage and an example of application thereof will be described with reference to blood dialysis treatment shown in FIG. 8. In the case of hemodialysis, usually shunts are used and accordingly the cuff 1 is attached to a part between the shunt 52 on the artery side and shunt 53 on the vein side. Therefore, a cuff of narrow width, for example ranging from 3 to 5 cm is used so as to permit easy fitting on the part between the two shunts. The blood flow passage 54 is provided with a membrane module 55 for dialyzing blood drawn through the shunt 51 on the vein side and a blood pump 56, and returns purified blood to the patient's body through the shunt 52 on the artery side. The numeral 58 indicates a flow passage for dialysate. A pillow switch 57 as a detector for detecting the negative pressure in the flow passage is disposed upstream of the pump 56. The pillow switch 57 comprises a pillow sensor 57a consisting of an inflatable/contractable bag-like band and a contact 57b which is in contact with the pillow sensor 57a and opened and closed with inflation and contraction, respectively, of the pillow sensor. When the quantity of drawn blood decreases during therapy, a negative pressure is generated by suctional force of the blood pump 56 in the flow passage between the shunt 51 on the vein side and the blood pump 56. The bag-like pillow sensor 57a of the pillow switch 57 contracts, as shown in the drawing, due to the abovesaid negative pressure, whereby the contact 57b is opened and negative pressure sensing signals are generated. In response to such sensing signals, the control circuit 20 acts for intermittently inflating the cuff. With intermittent pressing exerted on the patient's vein and the increase in quantity of drawn blood, the pillow sensor 57a returns to the initial state while inflating, and closes the contact 57b, thereby negative pressure sensing signals diminishing. In this way, the control device 20 becomes out of operation and the cuff contracts.

As described, an apparatus of this invention is suitable for extracorporeal blood treatment of all kinds. The apparatus, when the air discharge time is set at zero, permits continuous pressing and, therefore, provides optimum conditions for each individual patient, such as continuous pressing at the beginning of blood drawing and subsequent intermittent pressing.

What is claimed is:

1. A method from drawing blood from an arm or leg of a patient which comprises:
    inserting a blood-drawing needle into a vein in the arm or leg of a patient,
    winding a bag-like band around the patient's arm or leg, at a site downstream of the point of insertion of the blood-drawing needle, so as to increase the amount of blood drawn by said blood-drawing needle,
    inflating said bag-like band with air from a pneumatic pump so that said bag-like band presses tightly against the patient's arm or leg, and
    controlling the inflation of said bag-like band by:
        generating a periodic signal of 3-10 second duration which activates the closing of valve means concurrently with generating a first drive signal, followed by a 1-3 second period when neither signal is generated,
        monitoring the pressure is said bag-like band, such that a second drive signal is generated whenever the pressure is less than a reference value which is equal to 30-150 mm Hg, and
        monitoring said first and second drive signals such that a pump driving signal is generated activating said pneumatic pump only when said first and second drive signals are generated.

2. A method according to claim 1 further comprising:
    separating the plasma component from the corpuscular component of said blood using centrifugal force;
    removing toxic substances from said plasma component; and
    returning the purified plasma and said corpuscular component to the patient via a return blood needle.

3. A method according to claim 1 further comprising:
    separating the plasma component from the corpuscular component of said blood using a membrane;
    storing said plasma component in a bag;
    storing said corpuscular component in a bag; and
    monitoring the flow rate in the blood passage such that when said flow rate decreases, the corpuscular component is returned to the patient via said blood-drawing needle.

* * * * *